United States Patent
Marshall

(10) Patent No.: US 9,334,728 B2
(45) Date of Patent: May 10, 2016

(54) OIL WELL PRODUCTION ANALYZING SYSTEM

(71) Applicant: Dan W Marshall, Bakersfield, CA (US)

(72) Inventor: Dan W Marshall, Bakersfield, CA (US)

(73) Assignee: DWT Solutions, L.P., Bakersfield, CA (US)

( * ) Notice: Subject to any disclaimer, the term of this patent is extended or adjusted under 35 U.S.C. 154(b) by 310 days.

(21) Appl. No.: 14/157,446

(22) Filed: Jan. 16, 2014

(65) Prior Publication Data

US 2015/0198039 A1    Jul. 16, 2015

(51) Int. Cl.
*E21B 49/08* (2006.01)
*G01N 33/28* (2006.01)

(52) U.S. Cl.
CPC .......... *E21B 49/086* (2013.01); *G01N 33/2847* (2013.01)

(58) Field of Classification Search
CPC .............................. G01N 33/28; E21B 49/086
USPC ...................................................... 73/152.42
See application file for complete search history.

(56) References Cited

U.S. PATENT DOCUMENTS

| | | | |
|---|---|---|---|
| 4,924,695 A | 5/1990 | Kolpak | |
| 5,100,699 A * | 3/1992 | Roeser | B29B 7/749 118/302 |
| 5,211,842 A * | 5/1993 | Tuss | B01D 19/0015 166/75.12 |
| 5,251,488 A | 10/1993 | Haberman et al. | |
| 5,394,339 A | 2/1995 | Jones | |
| 6,032,539 A | 3/2000 | Liu et al. | |
| 6,272,906 B1 | 8/2001 | Fleury et al. | |
| 6,802,204 B1 | 10/2004 | Torkildsen | |
| 6,847,898 B1 * | 1/2005 | Chen | G01N 7/14 702/137 |
| 7,059,180 B2 * | 6/2006 | Al-Ghamdi | G01N 33/2823 702/12 |
| 8,056,400 B2 | 11/2011 | Reinjes et al. | |
| 8,245,572 B2 | 8/2012 | Birkett et al. | |
| 8,516,900 B2 | 8/2013 | Pihlaja et al. | |

* cited by examiner

*Primary Examiner* — Hezron E Williams
*Assistant Examiner* — Rodney T Frank
(74) *Attorney, Agent, or Firm* — James M. Duncan, Esq.; Klein DeNatale Goldner

(57) ABSTRACT

An oil well production analyzing system receives production fluid samples from the oil well according to an automated sampling schedule. The fluid samples are received within a degassing cylinder and separated into a liquid phase and a gas phase, with the liquid phase automatically transferred to a sampling cylinder for water cut analysis. Once the liquid phase has been transferred to the sampling cylinder, a piston within the degassing cylinder automatically evacuates all fluid from the cylinder in preparation of receiving a subsequent fluid sample from the oil well.

20 Claims, 3 Drawing Sheets

OIL WELL PRODUCTION ANALYZING SYSTEM

BACKGROUND OF THE INVENTION

The present invention generally relates to the on-sight analysis of fluids produced from hydrocarbon producing wells. In particular, the present invention relates to devices and methods which provide real-time determination of the relative components of the fluids produced from hydrocarbon producing wells. In this invention, phase separation and the determination of the relative volumes of each are accomplished by utilizing a pair of vessels in series, where the first vessel eliminates substantially all of the gas phase from a sample by actuation of a piston within the vessel which delivers a degasified sample to the second vessel which further processes the sample and delivers a liquid phase sample to a cut analyzer which ascertains the relative percentages of water and oil in the sample (i.e., the "cut" or "water cut").

An accurate real-time determination of water cut, when used in conjunction with other parameters such as oil gravity and gas liquid ratio, may be utilized to determine the real-time density of the produced fluid. Knowing the real-time density of the produced fluid may be utilized in conjunction with various devices, such as rod string load cells, to determine downhole pressures and real-time production rates. Knowing the water cut of individual wells on a real time basis also facilitates field wide reservoir analysis and management. For example, in a water flood operation, the detection of a sudden increase in a well's water cut provides useful information regarding the effectiveness of the flood.

The known cut analyzers are most accurate when analyzing a sample which does not have any free gas phase. Free gas in the sample typically results in under measurement of the water cut, so it is desirable to reduce or eliminate any free gas before analysis of the sample. Moreover, the presence of small, but unknown and variable amounts of entrained gases in the sample confound accurate fluid density measurement, which is critical to the extent that fluid density is an inputted variable for downhole monitoring and well diagnostics.

It is known that separation of the free gas phase from the liquid phase in a sample is desired prior to making a water cut determination is made. The American Society for Testing and Materials ("ASTM" and the American Petroleum Institute ("API") have provided a Standard Test Method for Water and Sediment in Crude Oil by the Centrifuge Method (D 4007) which provides a laboratory procedure for making water cut determinations. This method is generally accurate because, among other reasons, free gas has already separated from the oil. However, this operation is time consuming and requires manual processing of the sample. It is not a method which may be replicated in the field for real time determination of water cut. Instead, a number of various water cut meters are utilized. These meters utilize various operating principles and hardware to make the water cut determination, such as dielectric measurements using radio or microwave frequencies, optical detectors for detecting near infrared wavelengths, and gamma ray based instruments. It is to be noted that the presently disclosed invention can utilize almost any of the types of devices for the eventual water cut determination. The presently disclosed invention improves the accuracy of these devices by providing a sample, on the fly at real-time conditions, where the sample is essentially gas free and, optionally, heated to API standard temperature for water cut determination.

The common automated mechanisms for gas separation typically require large separators which typically rely upon heat, gravity, mechanical flow dividers (such as baffles), and relatively long holding times to sufficiently separate the gas phase from the liquid phase to obtain an accurate determination of the cut. While portable skid units having relatively smaller separation vessels are known, the accuracy of the water cut determination can be adversely impacted by the relatively small separator size and short time for separation.

SUMMARY OF THE INVENTION

The presently disclosed apparatus ascertains a relative percentage of water contained in a liquid phase of a fluid sample received from an oil well under real-time producing conditions. The fluid sample comprises a liquid phase and a gas phase, while the liquid phase comprises an oil component and a water component. The system has a fluid inlet which receives flow from a wellhead or production line from the well. The system also has one or more fluid outlets through which the fluid sample, after being analyzed, is discharged from the system. A plurality of vessels is disposed between the fluid inlet and the fluid outlet, typically in a series configuration, although a parallel configuration might also be utilized.

Among the vessels disposed between the fluid inlet and fluid outlet are a degassing cylinder and a sampling cylinder. The degassing cylinder is hydraulically connected to the sampling cylinder, typically in a series configuration. The degassing cylinder typically receives substantially all of the fluid sample from the fluid inlet. A piston is disposed within the degassing cylinder, with the piston being moveable from a first position to a second position. As the piston moves from the first position to the second position, substantially all of the liquid phase of the fluid sample is transferred to the sampling cylinder. This operation is similar to the operation of a plunger within a syringe displacing the contents of the syringe through the needle end of the syringe. Gas phase components are vented from the degassing cylinder during this process, where the gas phase may be gathered from the degassing cylinder. Gas gathered from the degassing cylinder and from the sampling cylinder may be commingled in a gathering line and measured through a gas flow meter, and if desired, a gas chromatograph to ascertain the gas stream constituents as discussed below. The gas flow meter may provide output to a digital processor.

The piston may be configured with a piston head and seals which efficiently sweep the cylinder clear of all fluids contained within the cylinder, such that there is little or no mingling of samples as each sample is processed through the system. The cylinder wall may be lined with a material which is non-stick and capable of receiving high temperature fluids.

Once the sample is transferred to the sampling cylinder, the sample may be heated to further effect separation of the liquid phase and gas phase, with gas phase components vented out of the sampling cylinder, where the gas phase may be commingled with the gas phase from the degassing cylinder as described above. The sample may be circulated through the sampling cylinder by a pump connected to an outlet of the sampling cylinder. A water cut analyzer as discussed above is hydraulically connected to the sampling cylinder, where the water cut analyzer receives a liquid sample from the sampling cylinder. The water cut analyzer generates data which allows the determination of the percentage of water, if any, within a liquid sample received from the sampling cylinder. The inventor herein has found that PHASE DYNAMIC water cut analyzers, which utilize the difference between the electrical characteristics of the water and oil to determine water content, are acceptable for use for water cut determination, but other water cut analyzers may be utilized as well.

In one embodiment, the sampling cylinder comprises a separate piston, similar to that of the degasing cylinder. In this embodiment, the fluid is swept from the sampling cylinder as this piston moves from a "raised" position to a "lowered" position. Fluid is discharged from the sampling cylinder as the piston moves from the raised to the lowered position. It is to be noted that, as utilized within this disclosure, the terms "raised," "lowered," "top," "bottom," etc., are made with respect to the orientations of the pistons and cylinders depicted in the figures herein. However, the operation of the system is not dependent upon the components of the system being oriented as depicted in the drawings. Therefore, the use of the terms "raised," "lowered," "top," "bottom," etc. should be understood to be consistent with the a "raised" piston being in the initial position before it sweeps a cylinder and a "lowered" piston being in its final position after it has swept the cylinder and cleared all fluid from the cylinder.

In one embodiment of the invention the degassing cylinder and/or the sampling cylinder may have sensors which ascertain the position of the piston within the degassing cylinder. For example, the sensors may detect when the piston is in the raised position, where there is a maximum volume of the cylinder available for inflowing fluid. The sensors may also detect when the piston is immediately adjacent to the bottom of the degassing cylinder, which is the position of the piston after it has swept all of the contents from the degassing cylinder. In another embodiment, the sampling cylinder and/or degassing cylinder may comprise heating means. The heating means will typically be of the electrical resistance type, such as heat blanketing wrapped about the sampling cylinder or the degassing cylinder. However, process heat might also be utilized with the sampling cylinder or the degassing cylinder configured with a heat exchanger receiving process fluids such as steam or heated liquids. For such embodiments, the sampling cylinder and/or degassing cylinder may be connected to one or more heat sensors which detect, or provide output which determines, the temperature of the fluid contained within the sampling cylinder and/or degassing cylinder.

It should be understood that all sensors utilized with embodiments of the device may be located outside of the degassing cylinder and the sampling cylinder, which greatly facilitates maintenance and repair. In addition, the sensors may be of the type which provide output signals compatible for receipt as input to a digital processor for either data collection or control purposes.

In another embodiment of the system, a vacuum may be applied to either the sampling cylinder and/or the degassing cylinder to facilitate the removal of gas phase components from the vessels. As discussed above, these gas phase components may be collected and piped through a flow meter to ascertain the relative volume of the gas phase in the sample. Additionally, the gas phase components may be processed through a gas phase analyzer, such as a chromatography unit. The vacuum may be either applied by a compressor integral to the system, or the vacuum may be applied from an external source, such as a field gas collection system.

The pistons in the degassing cylinder and the sampling cylinder may be actuated by various actuation devices, including low voltage servo motors. These motors may be actuated by the digital processor described above, such that a piston operating within the degassing cylinder is operating cooperatively with a piston operating within the sampling cylinder, according to conditions which may be detected by, among other things, the position sensors and temperature sensors described above, as well as flow sensors which may be utilized in the system. Among other possible input received by the processor and in addition to the other devices listed herein, the processor may also receive load information from a polish rod load cell, pressure transducers detecting the pressure of the degassing cylinder, the sampling cylinder, or downhole devices, water salinity from the water cut analyzer, gas flow rates from the gas flow meter, and other devices utilized in the industry.

The processor may therefore be utilized to manage the flow of a sample through the system, determining the time required to contain a satisfactory liquid sample for water cut determination, as well as controlling piston position, heat, etc. of the system. In addition, the processor may, based upon the data received through the gas meter, gas analyzer, water cut analyzer, etc., calculate a real time fluid density. Once known, the real time fluid density may be utilized in conjunction with a rod string load analyzer to ascertain flow rates and downhole flowing pressure.

DETAILED DESCRIPTION OF THE EMBODIMENTS

Figure 1:
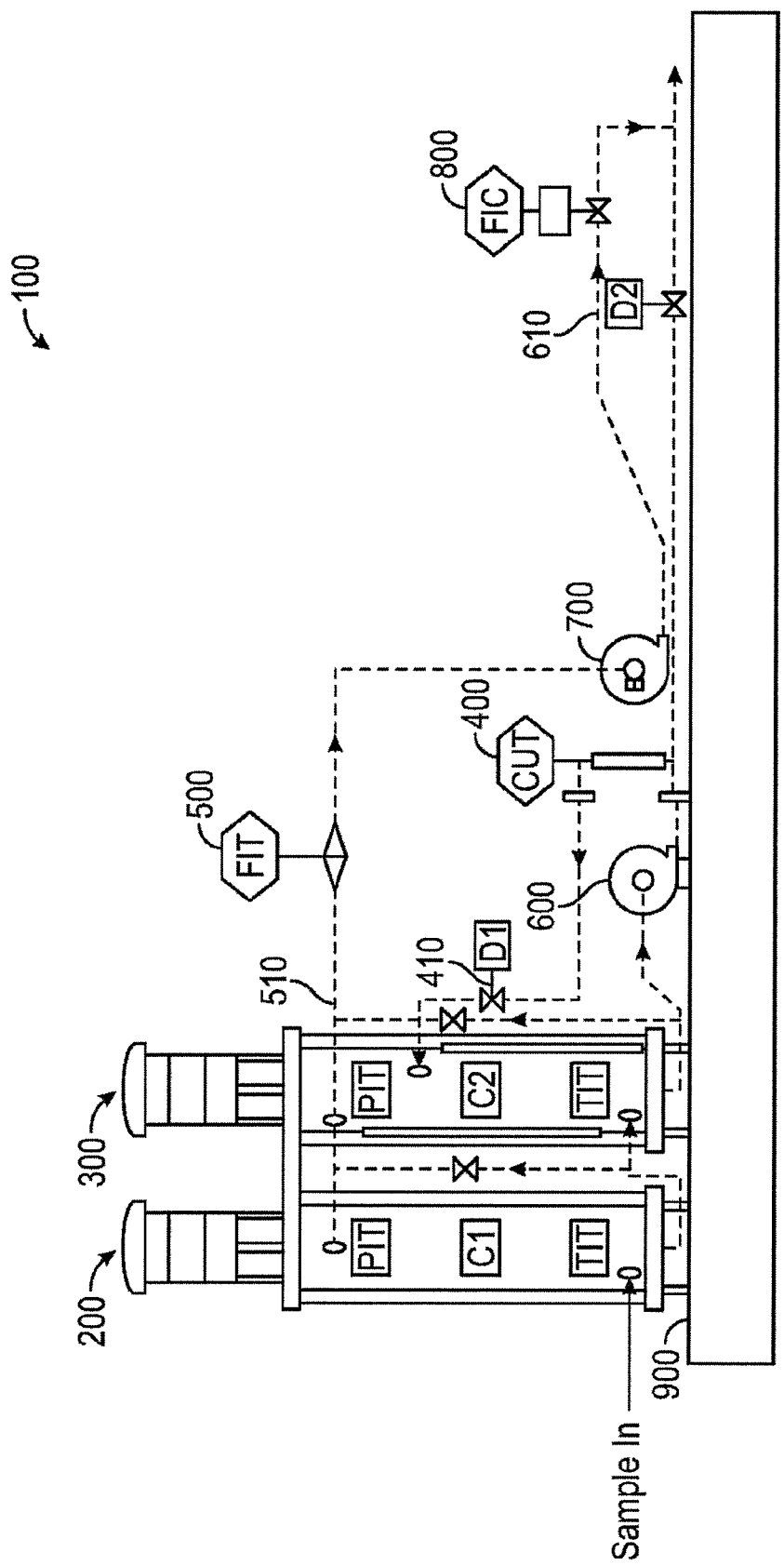
FIG. 1 shows a general schematic of an embodiment of the apparatus.

FIG. 1 schematically depicts an embodiment of the presently disclosed oil well production analyzing system 100 according to the present invention. The major components of this embodiment are degassing cylinder 200 and sampling cylinder 300. Additional components of this embodiment are water cut analyzer 400, gas flow meter 500, circulating pump 600, gas compressor 700, flow control valve 800, base member 900, and processor 1000. This production analyzing system will typically be connected at position close to an oil well, such that the received fluid sample received by the unit is essentially the same as produced at the wellhead from the well. The sample should be taken downstream of an inline mixer which is present in a flow-line coming from the oil well. An acceptable inline mixer is available through Automated Mechanical Process Systems Inc. of Bakersfield, Calif., part number DM-360. This inline mixer is configured in a spool piece which may be inserted within a well's production flow-line. For a 2 inch production flow-line, a 3 inch diameter spool is utilized, the spool having a length of approximately 23 inches. This in-line mixer comprises, in respective order from the upstream end: (1) a plurality of mixing vanes having both clockwise and counter-clockwise orientation; and (2) an internal conical structure with the small end of the cone facing upstream, the conical structure having a plurality (e.g., more than twenty) of axially-aligned slots through which the fluid flows.

It is to be appreciated that the components of the production analyzing system may be relatively small, fitting on a transportable skid for easy movement between locations. Flow volumes may be relatively small and interconnecting piping may be ½ inch stainless steel tubing.

Figure 2:
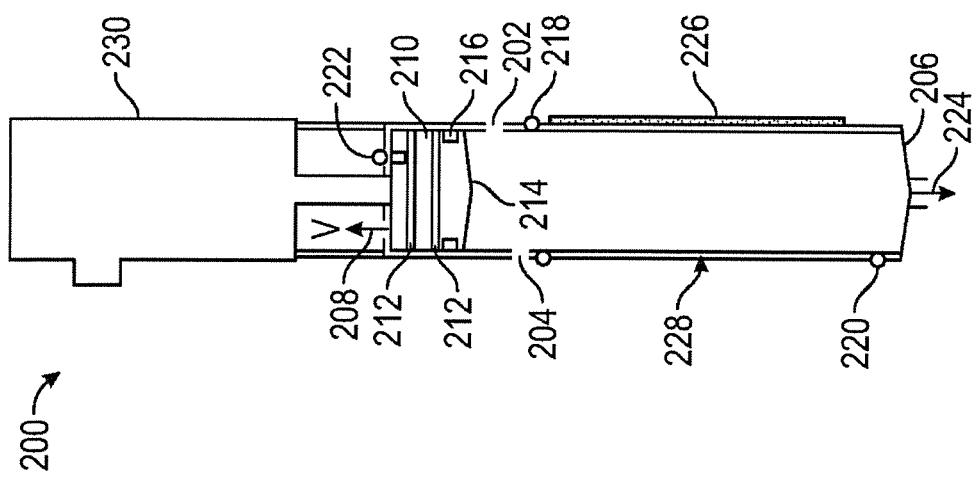
FIG. 2 shows an embodiment of a degassing cylinder and related components which may be used with the apparatus.

FIG. 2 schematically depicts an embodiment of a degassing cylinder 200 which may be utilized with the present system. The degassing cylinder 200 may be fabricated from 316 stainless steel and will typically be relatively small, perhaps having an outside diameter of 3 inches with an overall height (or length) of 36 inches, resulting in an approximate volume of 1.5 gallons of fluid. The internal surface of degassing cylinder 200 may be coated with a non-stick liner suitable for high temperature surface, which facilitates the removal of sample fluid from the cylinder 200. The degassing cylinder should be rated for a minimum of 300 psig, assuming a vacuum of 2.0 inches of water is applied to the vessel. The degassing cylinder 200 may be equipped with a rupture disc (not shown). Degassing cylinder 200 receives a fluid sample through inlet 202. Vent 204 provides for the outflow of gas phase components into a gas collection line 510 for transmission to gas flow meter 500.

Degassing cylinder 200 has a piston 210 which may have o-ring seals 212. The o-ring seals are typically configured as double seals having an adjustable wear backing ring. Piston 210 may have a head portion 214 which has a profile which mates with the profile of the bottom 206 of degassing cylinder 200, thereby providing for greater sweep efficiency of the degassing cylinder 200 by piston 210. Piston 210 may be actuated by a low voltage servo motor 230. The inventor herein has found that a 24 VAC, 1.6 amp, ¼ hp motor is suitable for this service.

Piston 210 may also have one or more displacement pick-ups 216. Displacement pick-ups 216 provide a signal which may be detected by displacement sensors such as a displacement sensor 218, piston down sensor 220, and piston up sensor 222. These sensors are positioned to receive signals from the displacement pick-ups when the piston 210 is adjacent to the sensors. The sensors may provide output signals which are conveyed to a processor 1000, which may be an industrial programmable controller or other processor capable of receiving, storing, and processing input data and providing output instructions based upon the input data. Degassing cylinder 200 may further comprise a means for heating the contents of the cylinder for both promoting gas separation as well as for pre-heating the fluid which is transferred to sampling chamber 300. The means for heating the cylinder may comprise an electrical resistance heating element, such as in a heat blanket 226 or it utilize process heat in conjunction with a heat exchanger receiving process fluids such as steam or heated liquids. The degassing cylinder 200 may be connected to one or more heat sensors 228 which detect the internal temperature of the degassing cylinder 200. Output from this sensor 228 may be conveyed to processor 1000.

As piston 210 sweeps the interior of degassing cylinder 200, liquid phase components are forced out of the cylinder through liquid outlet 224 and piped to the inlet of sampling cylinder 300. Gas phase components are released through vent 204 into a gas collection line 510 for transmission to gas flow meter 500. Gas separation may be further promoted by applying vacuum to vent 204 by connecting a vacuum line to the vent. For example vent 204 may be connected to the inlet of compressor 700 and a vacuum of a two inch water column applied to the inlet. As discussed below, sampling cylinder 300 has a similar vent 304 which flows into gas collection line 510. The commingled gas streams from the degassing cylinder 200 and the sampling cylinder 300 may flow through gas flow meter 500, pressurized by compressor 700 and returned into a group line as controlled by flow control valve 800.

Once the liquid phase and gas phase components of the fluid sample are cleared from degassing cylinder 200, piston 210 is raised to the upper portion of degassing cylinder 200, with any gas trapped between the piston 210 and the upper portion of the degassing cylinder allowed to escape through vent 208. Based upon input received by the processor 1000 regarding the completion of the cycle within the degassing cylinder 200 and the status of the of the liquid phase components in the sampling cylinder 300, the processor will issue instructions to a control valve (not shown) upstream of the degassing cylinder 200 to open and allow a new fluid sample to be received into the degassing cylinder to be processed in a new testing cycle.

Figure 3:
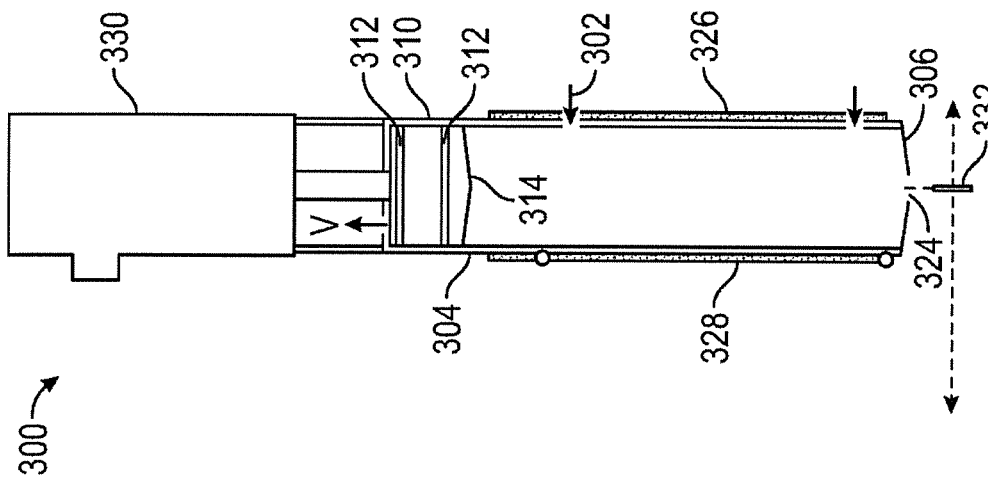
FIG. 3 shows an embodiment of a sampling cylinder and related components which may be used with the apparatus.

FIG. 3 schematically depicts an embodiment of a sampling cylinder 300 which may be utilized with the present system. For manufacturing and maintenance convenience, sampling cylinder 300 may be manufactured from similar materials as degassing cylinder 200, and have similar dimensions. Sampling cylinder 300 receives flow through inlet 302. Vent 304 provides for the outflow of gas phase components into a gas collection line 510 for transmission to gas flow meter 500. Sampling cylinder 300 is connected at outlet 324 to the intake of circulating pump 600. A sampling probe 332 may detect flowing liquid temperature at outlet 324 and provide this information to processor 1000.

Similar to degassing cylinder 200, sampling cylinder 300 may comprise a means for heating the contents of the cylinder. This heating will further promote separation of any free gas, and will also allow the liquid phase components to reach American Petroleum Institute ("API") standard temperatures for testing water cut through water cut analyzer 400. The means for heating the sampling cylinder 300 may comprise an electrical resistance heating element, such as in a heat blanket 326 or it utilize process heat in conjunction with a heat exchanger receiving process fluids such as steam or heated liquids. The degassing cylinder 300 may be connected to one or more heat sensors 328 which detect the internal temperature of the sampling cylinder 300.

Liquid phase components are circulated through water cut analyzer 400 which determines the relative percentages of water and oil in the circulating liquid phase. Water cut analyzer 400 may provide data output to processor 1000. Once stable and consistent water cut information is detected by the water cut analyzer 400, the circulation of the liquid phase through the circuit may be ceased by the issuance of instructions to a motor controller for circulating pump 600. Once circulation has stopped, automated valve 410 is closed and automated valve 610 is opened for return of the liquid phase components to the group line. Upon the completion of the water cut analysis, piston 310 may be actuated by servo motor 330 to clear any remaining fluid from sampling cylinder 300 for discharge from the disclosed oil well production analyzing system 100 and return to the group line and gathered with production from other wells.

Sampling cylinder 300 has a piston 310 which may have o-ring seals 312. Piston 310 may have a head portion 314 which has a profile which mates with the profile of the bottom 306 of sampling cylinder 300, thereby providing for greater sweep efficiency of the sampling cylinder 300 by piston 310. Piston 310 may be actuated by a low voltage servo motor 330 similar to that utilized with degassing cylinder 200, i.e., a 24 VAC, 1.6 amp, ¼ hp motor is suitable for this service.

Figure 4:
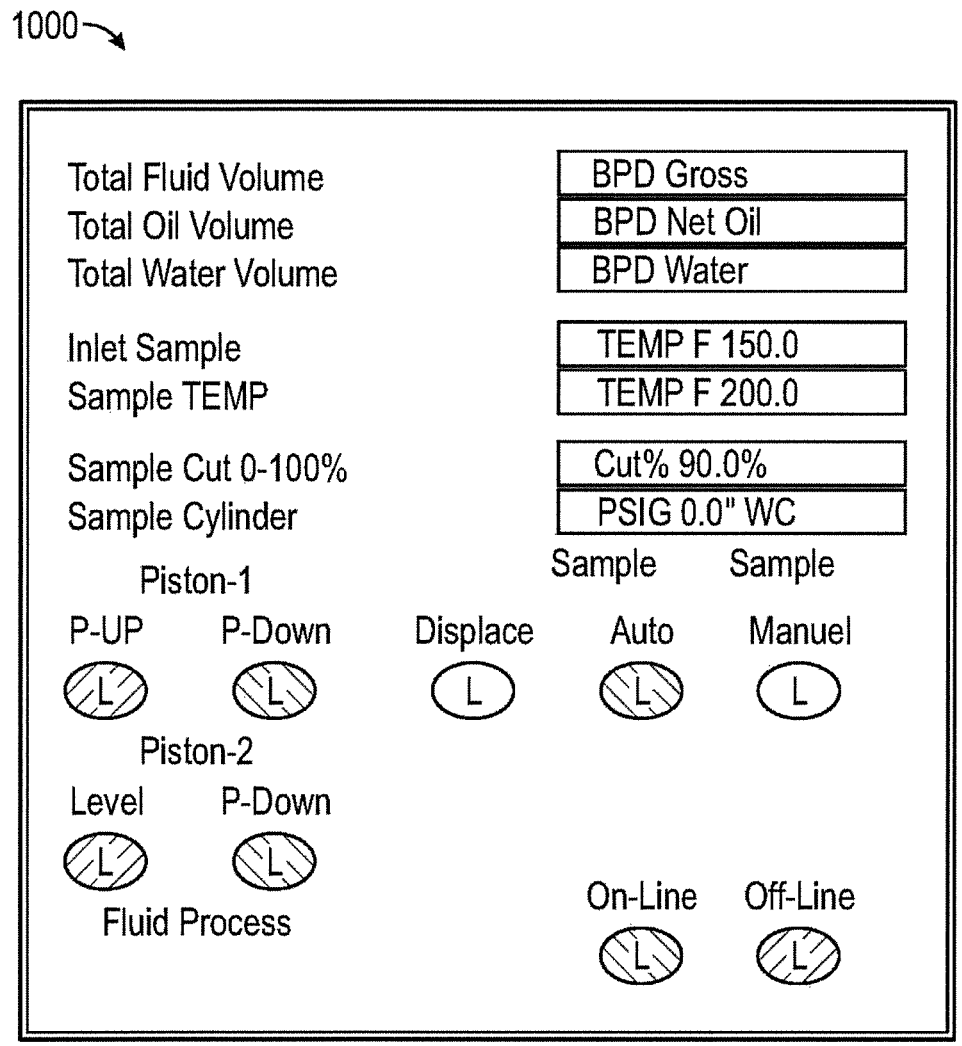
FIG. 4 exemplifies an operator screen of a digital processor which provides data display and/or control of embodiments of the disclosed apparatus.

FIG. 4 schematically shows a display from a digital processor 1000 which may be utilized with embodiments of the well production analyzing system 100. As exemplified by the schematic of FIG. 4, the processor display may show a calculated gross daily production rate, daily oil rate, and water rate, which would be calculated by the processor based upon input received from a load cell or other device. The processor may also display the water cut for a given sample, the temperatures of the fluid sample at the inlet of the device and the temperature of the liquid sample as it flows to the water cut analyzer 400. The processor may also display the current pressure and/or vacuum within the degassing cylinder 200 and the sampling cylinder 300. Control of the well production analyzing system 100 may also be performed at controls on the digital processor 1000, where the controls provide for manual or automated operation of the system, or allowing the system to be placed offline. The digital processor 1000 may provide a display which shows the status of the various components, such as the position of the pistons 210, 310 inside the degassing cylinder 200 and the sampling cylinder 300.

It is to be appreciated that the cycling of the oil well production analyzing system 100 is controlled by the processor 1000 based upon real time conditions observed through the various sensors and controlled through the actuation of various end devices as determined appropriate by the processor. Thus, the interaction of the degassing cylinder 200 and the sampling cylinder 300 and the various other end devices may be varied according to the observed conditions and as desired for the particular field. For example, the timing of the sampling and volume of produced fluid tested for a particular well may be adjusted as necessary to obtain consistent and representative information. the processor may, based upon the data received through the gas meter, gas analyzer, water cut analyzer, etc., calculate a real time fluid density. Once known, the real time fluid density may be utilized in conjunction with a rod string load analyzer to ascertain flow rates and downhole flowing pressure.

Appropriate piping for the oil well production analyzing system 100 is one half-inch stainless steel tubing with fittings, utilizing stainless steel ASCO solenoid and check valves. The oil well production analyzing system 100 may be configured as a compact skid package to facilitate transportation and installation of the unit. For example, the entire system may be configured into a unit 40 inches long by 40 inches tall by 30 inches wide.

While the above is a description of various embodiments of the present invention, further modifications may be employed without departing from the spirit and scope of the present invention. Thus the scope of the invention should not be limited according to these factors, but according to the claims to be filed in the forthcoming utility application.

What is claimed is:

1. A system for ascertaining a relative percentage of water contained in a liquid phase of a fluid sample received from a well, where the fluid sample comprises the liquid phase and a gas phase, and the liquid phase comprises oil and water, the system comprising:
a fluid inlet from the well through which the fluid sample is received, a fluid outlet through which the fluid sample is discharged, and a plurality of vessels disposed between the fluid inlet and the fluid outlet;
the plurality of vessels comprising a degassing cylinder and a sampling cylinder, wherein the degassing cylinder is hydraulically connected to the sampling cylinder, the degassing cylinder receiving at least a portion of the fluid sample from the fluid inlet;
a first piston disposed within the degassing cylinder wherein the first piston is moveable from a first position to a second position, wherein substantially all of the liquid phase of the fluid sample received by the degassing cylinder is transferred to the sampling cylinder as the first piston moves from the first position to the second position; and a water cut analyzer hydraulically connected to the sampling cylinder, the water cut analyzer adapted to receive a liquid sample from the sampling cylinder wherein the water cut analyzer provides data which may be utilized to determine a percentage of any water contained within the liquid sample received from the sampling cylinder.

2. The system of claim 1 wherein the degassing cylinder comprises a first sensor which ascertains when the first piston is in the first position and a second sensor which ascertains when the first piston is in the second position.

3. The system of claim 1 wherein the sampling cylinder comprises heating means.

4. The system of claim 3 wherein the heating means comprises a heat blanket.

5. The system of claim 3 wherein the sampling cylinder comprises a heat sensor for determining the temperature of fluid contained within the sampling cylinder.

6. The system of claim 1 wherein the sampling cylinder comprises a second piston moveable from a raised position to a lowered position, wherein fluid is discharged through the fluid outlet as the second piston moves from the raised position to the lowered position.

7. The system of claim 6 wherein the sampling chamber comprises an upper sensor which ascertains when the second piston is in the raised position and a lower sensor which ascertains when the second piston is in the lowered position.

8. The system of claim 1 wherein a vacuum is applied to the sampling cylinder to remove any gas phase from the sampling cylinder through a gas outlet.

9. The system of claim 8 wherein a flow meter is hydraulically connected to the gas outlet.

10. The system of claim 8 wherein the vacuum is applied by a compressor hydraulically connected to the gas outlet, the compressor discharging to the fluid outlet.

11. The system of claim 1 wherein the first piston is actuated by a low voltage servo motor.

12. The system of claim 6 wherein the second piston is actuated by a low voltage servo motor.

13. The system of claim 1 further comprising a processor which receives input from one or more sensors connected to the degassing chamber, the sampling chamber or the water cut analyzer.

14. The system of claim 13 wherein the processor provides output signals which cause the first piston to move between the first position and the second position.

15. The system of claim 14 wherein the first piston moves between the first position and the second position by a low voltage servo motor which receives the output signals from the processor.

16. The system of claim 13 wherein the sampling cylinder comprises a second piston moveable from a raised position to a lowered position and the processor provides output signals which cause the second piston to move between the raised position and the lowered position.

17. The system of claim 16 wherein the second piston moves between the raised position and the lowered position by a low voltage servo motor which receives the output signals from the processor.

18. A system for ascertaining a relative percentage of water contained in a liquid phase of a fluid sample received from a well, where the fluid sample comprises the liquid phase and a gas phase, and the liquid phase comprises oil and water, the system comprising:
a fluid inlet through which the fluid sample is received, a fluid outlet through which the fluid sample is discharged, and a plurality of vessels disposed between the fluid inlet and the fluid outlet;

the plurality of vessels comprising a degassing cylinder and a sampling cylinder, wherein the degassing cylinder is hydraulically connected to the sampling cylinder and the degassing cylinder receives at least a portion of the fluid sample from the fluid inlet;

a first piston disposed within the degassing cylinder wherein the first piston is moveable from a first position to a second position, wherein substantially all of the liquid phase of the fluid sample received by the degassing cylinder is transferred to the sampling cylinder as the first piston moves from the first position to the second position;

a second piston disposed within the sampling cylinder wherein the second piston is moveable from a raised position to a lowered position, wherein fluid is discharged through the fluid outlet as the second piston moves from the raised position to the lowered position;

a first sensor connected to the degassing cylinder which ascertains when the first piston is in the first position;

a second sensor connected to the degassing cylinder which ascertains when the first piston is in the second position;

an upper sensor connected to the sampling cylinder which ascertains when the second piston is in the raised position;

a lower sensor connected to the sampling cylinder which ascertains when the second piston is in the lowered position; and a digital processor which receives input from the first sensor, the second sensor, the upper sensor, and the lower sensor, wherein the digital processor provides instructions which control the positions of the first piston and the second piston.

19. The system of claim 18 further comprising a water cut analyzer hydraulically connected to the sampling cylinder, the water cut analyzer adapted to receive a liquid sample from the sampling cylinder wherein the water cut analyzer provides data which may be utilized to determine a percentage of any water contained within the liquid sample received from the sampling cylinder.

20. The system of claim 18 wherein the first piston moves between the first position and the second position by a first low voltage servo motor which receives the instruction from the processor and the second piston moves between the raised position and the lower position by a second low voltage servo motor which receives the instructions from the processor.

\* \* \* \* \*